US011883551B2

(12) United States Patent
Medvedev et al.

(10) Patent No.: US 11,883,551 B2
(45) Date of Patent: Jan. 30, 2024

(54) SYSTEMS AND METHODS FOR BULK STERILIZATION USING OZONE

(71) Applicant: OWS AGRI LIMITED, London (GB)

(72) Inventors: Dmitry Medvedev, Fort Worth, TX (US); Alex Tsipenyuk, Huntingdon Valley, PA (US)

(73) Assignee: OWS AGRI LIMITED, London (GB)

( * ) Notice: Subject to any disclaimer, the term of this patent is extended or adjusted under 35 U.S.C. 154(b) by 683 days.

(21) Appl. No.: 16/767,363

(22) PCT Filed: Jan. 30, 2018

(86) PCT No.: PCT/US2018/015846
§ 371 (c)(1),
(2) Date: May 27, 2020

(87) PCT Pub. No.: WO2019/151976
PCT Pub. Date: Aug. 8, 2019

(65) Prior Publication Data
US 2020/0384142 A1  Dec. 10, 2020

(51) Int. Cl.
*A61L 2/20* (2006.01)
*A61L 2/24* (2006.01)
(Continued)

(52) U.S. Cl.
CPC ............... *A61L 2/202* (2013.01); *A61L 2/24* (2013.01); *A61L 2/26* (2013.01); *G05D 7/0635* (2013.01);
(Continued)

(58) Field of Classification Search
CPC ... A61L 2/202; A61L 2/24; A61L 2/26; A61L 2202/11; G05D 7/0635; G05D 11/00
See application file for complete search history.

(56) References Cited

U.S. PATENT DOCUMENTS 3,700,468 A    10/1972  Shore et al.
4,507,253 A     3/1985  Wiesmann
(Continued)

FOREIGN PATENT DOCUMENTS

DE       4342624 C1    6/1995
KR    20010055638 A    7/2001

OTHER PUBLICATIONS

International Search Report and Written Opinion for the International Patent Application No. PCT/US18/15846, dated Mar. 29, 2018, 9 pages.

(Continued)

*Primary Examiner* — Sean E Conley

(57) ABSTRACT

A sterilization system may include an ozone generator, a buffer chamber, an ozone concentration monitor or cuvette, a treatment chamber, one or more valves, and a controller. The ozone generator generates a flow of ozone. The buffer chamber stores the flow of ozone. The ozone cuvette monitors a concentration of ozone from the buffer chamber. The treatment chamber receives a material for sterilization, and receives a flow of air/ozone. The controller selectively and independently controls each of the valves. The sterilization system including first and second operating modes. In the first operating mode, the treatment chamber is isolated from the ozone generator and the buffer chamber such that ozone is not being supplied to the treatment chamber. In the second operating mode, the treatment chamber is in communication with the ozone generator and the buffer chamber such that ozone is being supplied to the treatment chamber.

12 Claims, 3 Drawing Sheets

(51) Int. Cl.
  *G05D 7/06* (2006.01)
  *G05D 11/00* (2006.01)
  *A61L 2/26* (2006.01)
  *A61L 101/02* (2006.01)
  *A23L 3/3409* (2006.01)
  *A23L 3/3445* (2006.01)

(52) U.S. Cl.
  CPC ............ *G05D 11/00* (2013.01); *A23L 3/3445* (2013.01); *A23L 3/34095* (2013.01); *A23V 2002/00* (2013.01); *A61L 2101/02* (2020.08); *A61L 2202/11* (2013.01); *A61L 2202/122* (2013.01); *A61L 2202/14* (2013.01); *A61L 2202/15* (2013.01)

(56) References Cited

U.S. PATENT DOCUMENTS

| | | | |
|---|---|---|---|
| 4,549,477 | A | 10/1985 | McCabe |
| 4,732,480 | A | 3/1988 | Fortunato et al. |
| 5,334,355 | A | 8/1994 | Faddis |
| 5,420,432 | A | 5/1995 | Manook et al. |
| 5,632,333 | A | 5/1997 | Imamura et al. |
| 5,868,999 | A | 2/1999 | Karlson |
| 5,972,714 | A | 10/1999 | Roland et al. |
| 6,171,625 | B1 | 1/2001 | Denvir et al. |
| 6,485,769 | B2 | 11/2002 | Audy et al. |
| 6,518,574 | B1 | 2/2003 | Castleman |
| 6,673,248 | B2 | 1/2004 | Chowdhury |
| 6,764,659 | B2 | 7/2004 | Perlov et al. |
| 7,375,348 | B1 | 5/2008 | Sickenberger et al. |
| 8,298,418 | B2 | 10/2012 | Liechti et al. |
| 2001/0042843 | A1 | 11/2001 | Cox et al. |
| 2003/0030011 | A1 | 2/2003 | Brown et al. |
| 2004/0018630 | A1 | 1/2004 | Birks et al. |
| 2004/0052702 | A1 | 3/2004 | Shuman et al. |
| 2004/0097021 | A1 | 5/2004 | Augusto et al. |
| 2004/0241868 | A1 | 12/2004 | Cox et al. |
| 2005/0103723 | A1 | 5/2005 | Wilkins et al. |
| 2005/0160791 | A1 | 7/2005 | Kung |
| 2006/0240558 | A1 | 10/2006 | Zhao |
| 2008/0116054 | A1 | 5/2008 | Leach et al. |
| 2008/0304048 | A1 | 12/2008 | Tormod |
| 2009/0120473 | A1 | 5/2009 | Lynn |
| 2009/0302230 | A1 | 12/2009 | Birks et al. |
| 2010/0027016 | A1 | 2/2010 | Birks et al. |
| 2010/0061885 | A1 | 3/2010 | Harley |
| 2010/0159601 | A1 | 6/2010 | Patton |
| 2010/0212406 | A1 | 8/2010 | Browne et al. |
| 2011/0147580 | A1 | 6/2011 | Bell et al. |
| 2011/0164245 | A1 | 7/2011 | Eikelmann et al. |
| 2011/0201123 | A1 | 8/2011 | Watson et al. |
| 2012/0006098 | A1 | 1/2012 | Degner et al. |
| 2012/0135396 | A1 | 5/2012 | McDevitt et al. |
| 2013/0045496 | A1 | 2/2013 | Jansen |
| 2013/0270429 | A1 | 10/2013 | Bilenko et al. |
| 2013/0292581 | A1 | 11/2013 | Russell et al. |
| 2014/0034840 | A1 | 2/2014 | Davenport et al. |
| 2014/0106463 | A1 | 4/2014 | Wald et al. |
| 2015/0070889 | A1 | 3/2015 | Sooferian |
| 2015/0362426 | A1 | 12/2015 | Nishino et al. |
| 2015/0377772 | A1 | 12/2015 | Birks et al. |
| 2016/0103089 | A1 | 4/2016 | Boyette et al. |
| 2016/0187214 | A1 | 6/2016 | Al-Hemyari |
| 2017/0115272 | A1 | 4/2017 | Rihani et al. |
| 2017/0219479 | A1 | 8/2017 | Bilenko et al. |
| 2019/0056317 | A1 | 2/2019 | Clausen et al. |

OTHER PUBLICATIONS

International Search Report and Written Opinion for the International Patent Application No. PCT/US18/13797, dated May 10, 2018, 7 pages.

International Search Report and Written Opinion for the International Patent Application No. PCT/US18/015019, dated Apr. 6, 2018, 10 pages.

International Search Report and Written Opinion for the International Patent Application No. PCT/US18/14768, dated Apr. 5, 2018, 8 pages.

Nikoleav et al., "Atmospheric Ozone Concentration Measurement by UV Light-Emitting Diode Radiation Absorption" Bulletin of the Lebedev Physics Insitute. 2013, vol. 40 (2), pp. 50-53.

International Search Report and Written Opinion for the International Patent Application No. PCT/US18/14841, dated Mar. 29, 2018, 8 pages.

International Search Report and Written Opinion for the International Patent Application No. PCT/US18/17601, dated May 7, 2018, 7 pages.

SYSTEMS AND METHODS FOR BULK STERILIZATION USING OZONE

This is a national stage application filed under 35 U.S.C. § 371 of pending international application PCT/US2018/015846, filed Jan. 30, 2018, the entirety of which application is hereby incorporated by reference herein.

FIELD OF THE DISCLOSURE

The present disclosure relates generally to sterilization systems and methods, and more particularly to a system and method for laboratory testing and refinement of parameters of developed equipment for bulk sterilization using ozone.

BACKGROUND OF THE DISCLOSURE

In the food industry avoiding bacterial contamination is a major concern. To treat this problem, various sterilizing chemical agents, such as formaldehyde, glutaraldehyde, chlorine, and other processes, such as heat and radiation, are used to kill these harmful microorganisms. These techniques however have various negative or undesirable effects on safety, environmental and food quality, and taste.

Use of ozone can solve the problem of sterilization without these negative effects, but to develop ozone sterilization equipment, one needs to have reliable information about key parameters of the installation. In particular, two key parameters are ozone concentration and treatment time. Unfortunately, these parameters strongly depend on other factors such as humidity, temperature, and the nature of products to be treated.

In order to properly evaluate ozone concentration and treatment time to be used for industrial sterilization equipment, laboratory tests have to be made with certain food products. During these tests precise control of ozone concentration, temperature, and humidity during the treatment time has to be maintained.

It is with respect to these and other considerations that the present improvements may be useful.

SUMMARY

This summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is an improved sterilization system. The sterilization system may include an ozone generator for generating a flow of ozone. A buffer chamber in fluid communication with the ozone generator for storing the flow of ozone received from the ozone generator. An ozone cuvette in fluid communication with the buffer chamber for monitoring a concentration of ozone in a flow of ozone passing from the buffer chamber to the ozone cuvette. A treatment chamber for receiving a material for sterilization. The treatment chamber being in fluid communication with the ozone cuvette for receiving a flow of ozone from the ozone cuvette. One or more valves coupled between the buffer chamber and the ozone cuvette, and between the ozone cuvette and the treatment chamber, each valve being selectively movable between an open position and a closed position. A controller in communication with the one or more valves for selectively and independently moving each of the valves between the open and closed positions. The sterilization system includes first and second operating modes. In the first operating mode, the treatment chamber is isolated from the ozone generator and the buffer chamber such that ozone is not being supplied to the treatment chamber. In the second operating mode, the treatment chamber is in communication with the ozone generator and the buffer chamber such that ozone is being supplied to the treatment chamber.

The ozone cuvette may be communicatively coupled to the controller such that when the controller determines that an ozone concentration of the flow of ozone received by the ozone cuvette from the buffer chamber is equal to or greater than a predetermined concentration, the controller transitions the sterilization system from the first operating mode to the second operating mode.

In the first operating mode, the controller may selectively close an ozone injection valve coupled between the ozone cuvette and the treatment chamber so that the flow of ozone to the treatment chamber is prevented. In addition, the controller may further selectively open an ozone bypass valve coupled between the ozone cuvette and an ozone destructor so that the flow of ozone passes through the ozone destructor and then into the atmosphere.

In the second operating mode, the controller may selectively close the ozone bypass valve and selectively open the ozone injection valve so that ozone flows to the treatment chamber.

In one embodiment, the controller may be programmed to execute instructions to control a flow rate of the flow of ozone, a flow rate of air being mixed with the flow of ozone, a temperature of the air, and a humidity of the air. The controller may be programmed to execute instructions to automatically adjust the flow rate of the flow of ozone, the flow rate of air being mixed with the flow of ozone, the temperature of the air, and the humidity of the air to maintain a desired concentration and flowrate of the flow of ozone into the treatment chamber.

The sterilization system may further include an air source for supplying a flow of air to the ozone generator, the ozone generator for converting the flow of air into the flow of ozone. The air source may include a cylinder of compressed air and a concentrator to increase a level of oxygen in the flow of oxygen supplied to the ozone generator.

In the first operating mode, the ozone generator may operate continuously to supply the buffer chamber with the flow of ozone.

In one embodiment, a concentration of the flow of ozone stored in the buffer chamber is greater than a concentration of ozone provided to the treatment chamber. For example, the concentration of the flow of ozone in the buffer chamber may be approximately 10 times greater than the ozone concentration of the flow of ozone provided to the treatment chamber.

The ozone cuvette may continuously sense the concentration of the flow of ozone being supplied by the buffer chamber and provide sensed concentration information to the controller.

The sterilization system may further include an ozone destructor to convert the flow of ozone back into oxygen.

In the first operating mode, the flow of ozone may flow from the ozone cuvette to a second valve to an ozone bypass valve to an ozone destructor. In the second operating mode, a flow of air may be supplied to an air supply line in communication with the treatment chamber.

The sterilization system may further include a blower and a flow meter coupled to the line of air for controlling a flow rate of the flow of air. In addition, the system may include a humidifier and an air cooler in fluid communication with the air supply line for monitoring and controlling a humidity and a temperature, respectively, of the air. Furthermore, the system may include a flow control valve disposed in the air supply line, the flow control valve positioned downstream of the humidifier, the air cooler, the blower and the flow meter.

Also disclosed herein is a method for sterilizing a material. The method including placing the material to be sterilized in a treatment chamber, generating a flow of ozone, storing the flow of ozone in a buffer chamber, monitoring a concentration of ozone in the flow of ozone exiting the buffer chamber, and selectively controlling one or more valves positioned between the buffer chamber and the treatment chamber to transition between first and second operating modes. In the first operating mode, the flow of ozone is not provided to the treatment chamber. In the second operating mode, the flow of ozone is directed into the treatment chamber for sterilizing the material.

In one embodiment, the method may also include determining that the concentration of ozone in the flow of ozone is equal to or greater than a predetermined concentration, and upon determining that the concentration of ozone in the flow of ozone is equal to or greater than the predetermined concentration, transiting from the first operating mode to the second operating mode.

In one embodiment, the method may also include selectively closing an ozone injection valve positioned between the buffer chamber and the treatment chamber so that the flow of ozone to the treatment chamber is prevented, and selectively opening an ozone bypass valve so that the flow of ozone flows into atmosphere.

In one embodiment, the method may also include selectively closing the ozone bypass valve, and selectively opening the ozone injection valve so that ozone flows to the treatment chamber.

BRIEF DESCRIPTION OF THE DRAWINGS

By way of example, exemplary embodiments of the disclosed device will now be described, with reference to the accompanying drawings, in which.

DETAILED DESCRIPTION

The following disclosure is intended to provide exemplary embodiments of the disclosed system and method, and these exemplary embodiments should not be interpreted as limiting. One of ordinary skill in the art will understand that the steps and methods disclosed may easily be reordered and manipulated into many configurations, provided they are not mutually exclusive. As used herein, "a" and "an" may refer to a single or plurality of items and should not be interpreted as exclusively singular unless explicitly stated.

Ozone ($O_3$) can be a highly effective sanitizer for treating contaminants such as *E-coli, listeria, salmonella*, and *campylobacter*. Further, the strong oxidizing properties of ozone can destroy a wide range of pathogens, including fungi and prions. Ozone may be applied during food processing to safely sanitize the food and/or food processing environment.

Ozone offers many advantages as a sterilant gas. It is a very efficient sterilant because of its strong oxidizing properties capable of destroying a wide range of pathogens, including fungi and prions, without the need for handling hazardous chemicals since the ozone is generated at the point of use from oxygen. The high reactivity of ozone means that waste ozone can be quickly destroyed by, for example, passing over a simple catalyst that reverts the ozone back to oxygen and ensures that cycle time is relatively short. Ozone can be applied during food processing in either a gaseous form or a liquid spray.

Ozone can be used during food processing because of its strong ability to kill bacteria and microorganisms. Its effectiveness is much greater than that of other sanitizing agents and it can be applied during any stage throughout the course of production. Ozone is able to destroy a wider variety of organisms than other cleaning agents, such as chlorine or formaldehyde, without creating harmful by-products that could be potentially dangerous. The exposure treatment time for ozone, is also considerably lower than those of other treatment methods. It is for these reasons that ozone is a preferred choice as a disinfecting agent.

Gaseous ozone can be used in, for example, poultry sheds or hatcheries to reduce or eliminate disease causing pathogens to ensure the animals grow healthy. It can also be used to sanitize contaminated surfaces along the flow of livestock processing. Other implementations include the sterilization of entire rooms, warehouses, truck boxes, and other enclosures that can be used to store food products and/or other objects or surfaces to be sterilized using an ozone-containing atmosphere.

Figure 1:
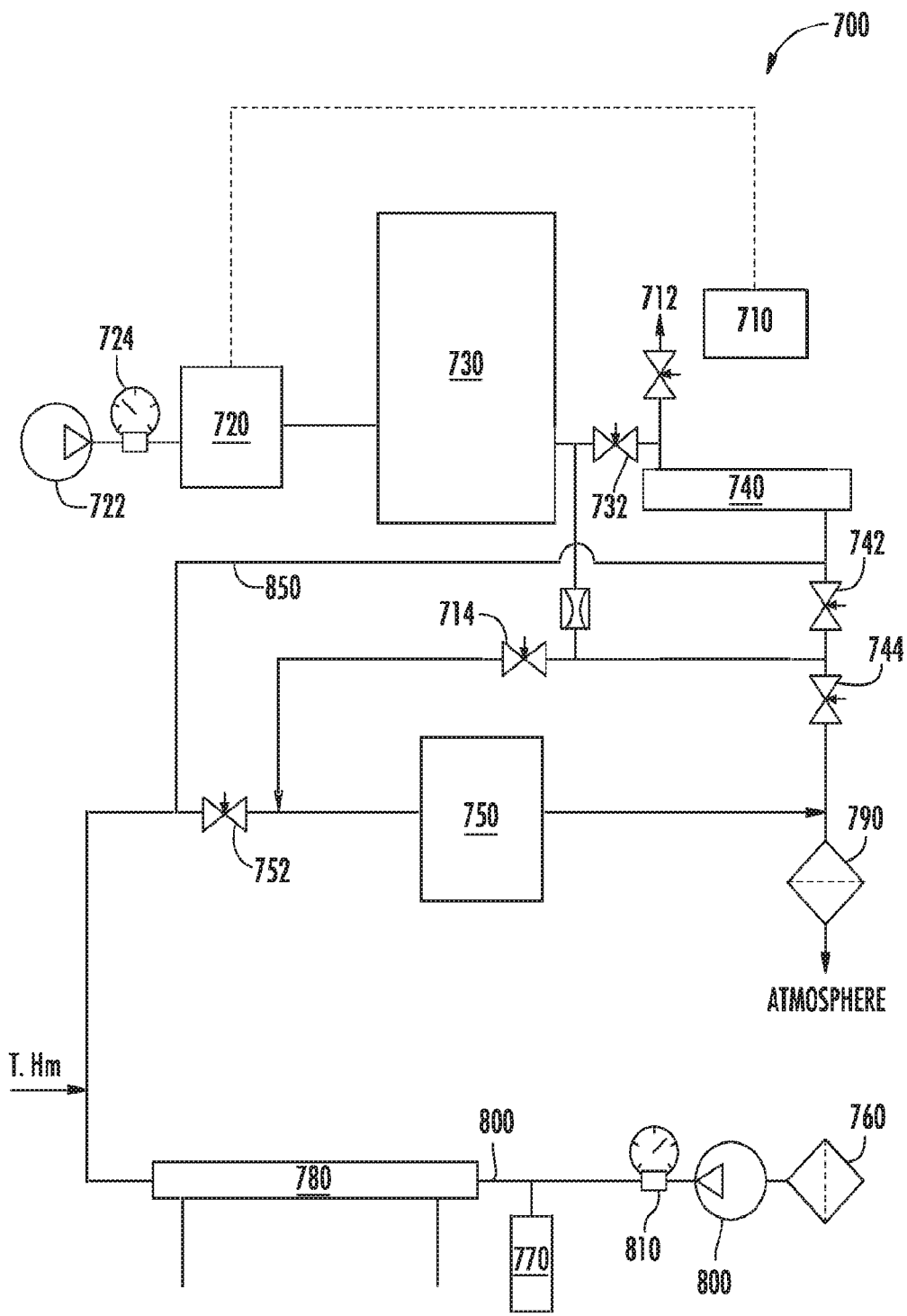
FIG. 1 is a system diagram illustrating an exemplary embodiment of a system flow for a sterilization system.

Referring now to FIG. 1, an exemplary embodiment of a sterilization system 700 consistent with a non-limiting, exemplary embodiment of the present disclosure is shown. The sterilization system 700 may be used to decontaminate material via an air flow containing a desired concentration of ozone.

As previously mentioned, ozone (03) can be a highly effective sanitizer/decontaminant for treating contaminants and for destroying a wide range of pathogens. Specifically, ozone can be applied during food or animal feed processing to safely sanitize the food and/or the food processing environment. However, to be effective, the treatment conditions within the treatment chamber should be effectively controlled to provide a desired concentration of ozone. To effectively control the ozone concentration in the treatment chamber, it would be beneficial to precisely control one or more aspects such as the flow rate of the ozone, the flow rate of air to be mixed with the ozone, the temperature of the supplied air, the humidity of the supplied air, etc. To this end, it is desirable to provide an ozone treatment system that can selectively and independently control all of these parameters to ensure that a sufficient concentration of ozone interacts with the bulk material (e.g., food, animal feed, etc.) placed within the treatment chamber. Preferably, the treatment system 700 is computer controlled so that automatic adjustments of these parameters can be achieved, thus facilitating a desired set of conditions in the treatment chamber.

FIG. 1 shows a sterilization system 700 including a controller 710 and an ozone generator 720 coupled to a buffer chamber 730 for storing and discharging a desired concentration of ozone. An ozone cuvette 740 may be coupled to the discharge of the buffer chamber 730 to monitor the concentration of ozone within the buffer chamber 730 (and being discharged from the buffer chamber 730). A treatment chamber 750 may be coupled downstream of the ozone cuvette 740. As will be appreciated the treatment chamber 750 may be suitably sized to contain a quantity of material to be sanitized/decontaminated.

In use, the controller 710 may be located within the sterilization system 700. In one embodiment, before commencing a test, an operator may input a desirable treatment time via, for example, a timer. Before commencing the test, the bulk material (e.g., food, animal feed, etc.) may be placed within the test chamber 750 and the lid of the test chamber 750 is closed. Next, the test may be commenced via, for example, pressing a "START" button on the controller 710. As will be described in greater detail below, during testing or treatment, an ozone bypass valve 744 may be in a closed position, while an ozone injection valve 714 may be in an opened position. As a result, within a short period of time, (e.g., a few seconds), the ozone concentration within the test chamber 750 reaches a desired level. Treatment may be automatically completed upon completion of the desired treatment time. Alternatively, treatment may be completed by, for example, manually pushing a "STOP" button on the controller 710. In either event, upon completion of the treatment, the ozone injection valve 714 may be closed and the ozone bypass valve 744 may be opened resulting in the ozone concentration within the test chamber 750 dropping to zero within a short period of time (e.g., a few seconds).

As will be described in greater detail later, air may be mixed with a flow of ozone discharged from the buffer chamber 730 so as to provide a desired final concentration of ozone in the treatment chamber 750. As will be further described, this air flow (along with the ozone flow) can be carefully controlled to provide a desired set of characteristics within the treatment chamber 750 (e.g., ozone concentration, humidity, temperature, gas flow rate through the chamber, and the like). Thus, the sterilization system 700 may include an air in-take 760, a humidifier 770, an air cooler 780, and any number of flow meters, valves, etc., to enable adjustment of the aforementioned parameters in a controllable way, as will be described in greater detail below.

The ozone generator 720 may be configured to convert the air flow from the air source 722 into ozone flow. This can be accomplished by splitting some oxygen ($O_2$) in the air flow into atomic oxygen (O). The atomic oxygen (O) may then bond with another oxygen ($O_2$) in the air flow to form ozone ($O_3$). In some embodiments, the air flow may be converted into ozone flow by exposing the air flow to electromagnetic radiation (e.g. UV light) or a plasma (e.g. electric arc). The ozone flow may be exhausted from the ozone generator 720 as ozone flow, and may be directed in a manner desired to one or more components of the system 700. In some non-limiting exemplary embodiments, the ozone flow may be from about 0.1 gm/hr to about 2,500 gm/hr.

In use, as will be described in greater detail below, the controller 710 may be in communication with any or all of the other components in the sterilization system 700 such that the controller 710 is capable of receiving information from any or all of the various components (e.g., meters, cuvettes, sensors, etc.). In addition, based on the received information, the controller 710 is preferably capable of selectively and independently controlling any or all of the components in the stabilization system 700, for example, the controller 710 is preferably capable of selectively and independently opening or closing any one of the valves in the system 700 based on a mode of the system (e.g., startup mode, treatment mode) and/or any information received from any of the connected sensors of the system. As will be appreciated by one of ordinary skill in the art, the controller 710 may include a processor, memory, control logic, displays, inputs and any other elements appropriate for achieving the objectives of the system.

Figure 2:
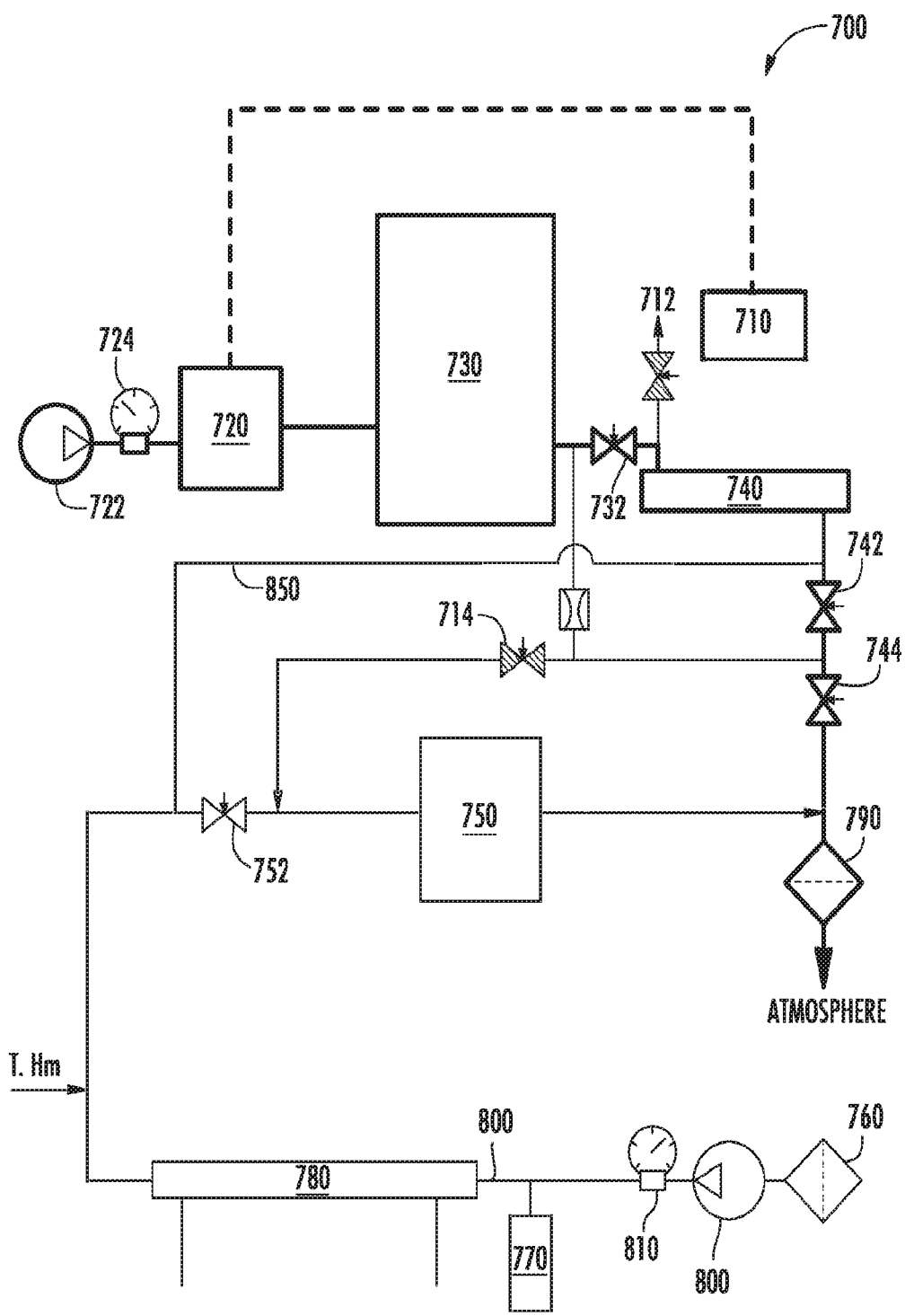
FIG. 2 is a system diagram illustrating a first operating mode of the exemplary embodiment of the sterilization system shown in FIG. 1.

The sterilization system 700 may include first and second operating modes. The first operating mode may also be referred to herein as a start-up mode, while the second operating mode may be referred to herein as a treatment mode. Referring to FIG. 2, the first operating mode is illustrated. As shown, the first operating mode or start-up operating mode may be used initially (e.g., when the system is started) to ensure that there is a sufficient concentration of ozone generated prior to the ozone being directed to the treatment chamber 750, where it will interact with the material. In connection with the sterilization system 700, it is envisioned that the treatment chamber 750 may be a dry chamber where material, such as, for example, food, animal feed, food processing equipment, etc. may be placed so that a desired concentration of ozone gas may sanitize and decontaminate the material. However, it is envisioned, that in some embodiments the treatment chamber 750 may also be in the form of a wet chamber, or a combination dry and wet chamber.

In the first or start-up operating mode, the controller 710 closes discharge valve 712 and ozone injection valve 714. In addition, the controller 710 opens a first isolation valve 732, a second isolation valve 742 and ozone bypass valve 744. In this manner, the controller 710 isolates the ozone generator 720 and the buffer chamber 730 from the treatment chamber 750. As such, in the first or start-up operating mode, ozone is not supplied to the treatment chamber 750. For convenience of description, FIG. 2 shows, in the highlighted regions, the flow path of gas through the system 700 during the first or start-up operating mode.

The controller 710 may initiate operation of the ozone generator 720. As previously mentioned, the ozone generator 720 may receive an air flow from an air source 722. In some embodiments, the air source 722 may include a cylinder of compressed air. In other embodiments, the air source 722 may an air compressor. In various such other embodiments, the air source 722 may include a concentrator to increase a level of oxygen in the air flow supplied to the ozone generator 720. In addition, a flow meter 724 may be coupled between the air source 722 and the ozone generator 720 for controlling the rate of air being fed to the ozone generator 720. In one embodiment, the air source 722 may supply approximately 1 cubic meter of air to the ozone generator 720.

In use, the ozone generator 720 is preferably capable of adjusting the amount of ozone being discharged therefrom. In this manner, the system 700 can adjust the ozone concentration in the treatment chamber 750 (e.g., during the second or treatment operating mode, as will be described in greater detail below).

The ozone generator 720 may be configured to convert the air flow into an ozone flow by any appropriate technology either now known or hereafter developed, as previously described. In the sterilization system 700, the ozone generator 720 preferably supplies ozone to the buffer chamber 730 where the ozone may be stored or charged. In one embodiment, the ozone generator 720 may continuously operate to continuously supply the buffer chamber 730 with a supply of ozone. In addition, in one embodiment, the concentration of ozone in the buffer chamber 730 is greater than the concentration of ozone desired within the treatment chamber 750. In one embodiment, the concentration of ozone in the buffer chamber 730 may be approximately 10 times the concentration of the ozone needed for the treatment chamber 750, although this comparison is merely exemplary and is not limiting. One of ordinary skill in the art will understand that the buffer chamber 730 may contain any concentration of ozone desired to provide an appropriate concentration of ozone in the treatment chamber 750 for sterilizing and/or decontaminating materials placed therein. Preferably, the concentration of ozone exiting the ozone generator 720 is monitored by the controller 710, which in one embodiment, may act as both as an ozone meter and a controller. It will be appreciated that in some embodiments a separate ozone meter may provide information to the controller to enable the controller to monitor and control the ozone generator in response thereto. Furthermore, the amount of ozone produced by the ozone generator 720 may be adjusted based on readings from the controller 710.

Ozone stored in the buffer chamber 730 may be supplied to the ozone cuvette 740 via the first isolation valve 732, which was rendered opened by the controller 710. In use, the ozone cuvette 740 monitors the concentration of ozone being discharged by the buffer chamber 730 (i.e., it monitors the concentration of ozone in the buffer chamber). The ozone cuvette 740 preferably is always functioning so that it can constantly measure the concentration of ozone flowing from the buffer chamber 730. Once the controller 710 determines (from information signals received from the ozone cuvette 740) that the concentration of ozone being supplied by the buffer chamber 730 is of a desired predetermined concentration, or within a desired predetermined range of concentrations, the first or start-up operating mode is complete.

It should be noted that during the first or start-up mode, ozone gas may be discharged to the atmosphere via an ozone destructor 790. As shown, in one embodiment, ozone may flow from the ozone cuvette 740 to the second isolation valve 742 to ozone bypass valve 744 to the ozone destructor 790.

As previously mentioned, the ozone destructor 790 may be configured to convert ozone back into oxygen. The ozone destructor 790 may be configured to remove toxicity from the exhaust flow before it is emitted into the atmosphere. In various embodiments, the ozone destructor 790 may receive an exhaust flow with high levels of ozone from the ozone cuvette 740 (in the first or start-up operating mode) or from the treatment chamber 750 (in the second or treatment operating mode, as will be described in greater detail below). The ozone destructor 790 may be configured to convert ozone in the exhaust flow back into oxygen. The oxygen may then be released back into the atmosphere. By converting ozone back into oxygen before releasing it into the atmosphere, pollution generated by the sterilization system 700 can be reduced or eliminated. The ozone destructor 790 may be any device or method now known or hereafter developed for the purposes of converting ozone to oxygen. For example, the ozone destructor 790 may expose ozone to a catalyst, causing the ozone ($O_3$) to lose an atomic oxygen (O) and to revert back to oxygen ($O_2$) for release into the atmosphere. The atmosphere may refer to the earth's atmosphere, the atmosphere within an enclosed space such a building, or the like. In some embodiments, the ozone destructor 790 may include a carbon filter.

As previously mentioned, once the ozone cuvette 740 determines that the concentration of ozone being supplied by the buffer chamber 730 is of sufficient concentration, the first or start-up operating mode is complete. At this point, the second or treatment operating mode may commence.

Figure 3:
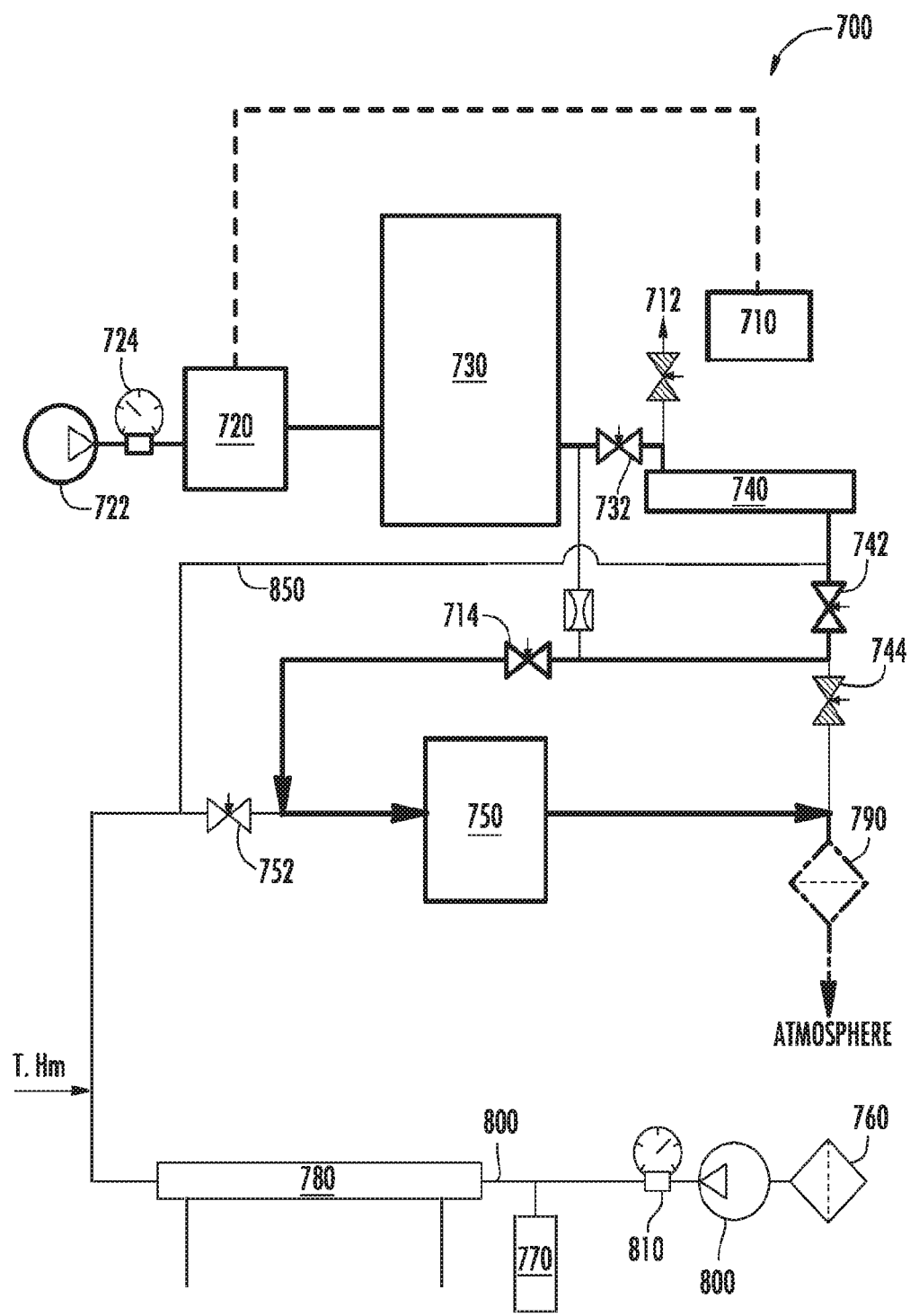
FIG. 3 is a system diagram illustrating a second operating mode of the exemplary embodiment of the sterilization system shown in FIG. 1.

Referring to FIG. 3, in the second or treatment operating mode, the controller 710 closes discharge valve 712 and ozone bypass valve 744. In addition, the controller 710 opens valve the first isolation valve 732, the second isolation valve 742, the ozone injection valve 714, and the flow control valve 752. In this manner, the treatment chamber 750 is no longer isolated from the ozone generator 720 and the buffer chamber 730. As such, the treatment chamber 750 is now being supplied with an air/ozone mixture. For convenience of description, FIG. 3 shows, in the highlighted regions, the flow path of gas through the system 700 during the second or treatment operating mode.

Similar to the first or start-up operating mode, in the second or treatment operating mode, the ozone generator 720 is preferably supplying ozone to the buffer chamber 730 where the ozone may be stored and discharged to the treatment chamber 750. The ozone from the buffer chamber 730 is supplied to the ozone cuvette 740 via the first isolation valve 732, which was opened by the controller 710. However, when the system 700 (e.g., the ozone cuvette 740 and/or controller 710) monitors the concentration of ozone being discharged from the buffer chamber 730 and determines that the concentration of ozone being supplied by the buffer chamber 730 is of sufficient concentration, the ozone is supplied to the treatment chamber 750 via ozone injection valve 714, which was also opened by the controller 710. As will be described in greater detail below, the ozone is supplied to an air supply line 800 that is connected to the treatment chamber 750. In the illustrated embodiment ozone is inputted to the air supply line 800 at a tee or other appropriate connection located downstream of the flow control valve 752. The ozone is mixed with air, preferably air having a desired temperature, humidity and flow rate, prior to entering the treatment chamber 750. In non-limiting exemplary embodiments, the ozone is supplied to the air supply line 800 at a concentration of approximately 0 to 10 parts per million (ppm), and at a flow rate of from 0.1 to 2 cubic feet per minute (CFM).

As will be appreciated, the size (i.e., diameter) of the air supply line 800 may be selected to ensure that turbulent flow within the line will cause a desired mixing of the ozone and air prior to the mixture entering the treatment chamber 750. Although not illustrated, it is contemplated that mixing devices could, in some embodiments, be employed to ensure a desired mixing of ozone and air being supplied to the treatment chamber 750.

In the second or treatment operating mode, air is preferably being supplied to the air supply line 800 via an air in-take 760. As such, the air in-take 760 is in fluid communication with the air supply line 800. The air in-take 760 may include a filter for filtering out dust and other air-born particles from the atmospheric air. The sterilization system 700 may include a blower 800 and a flow meter 810 coupled to the air supply line 800 for supplying and controlling the flow rate of air provided via the air supply line. In one non-limiting exemplary embodiment, the air may be supplied at approximately 8 to 10 cubic meters per hours, more preferably approximately 9 cubic meters per hour.

The sterilization system 700 may further include a humidifier 770 and an air cooler 780 for monitoring and controlling the humidity and temperature, respectively, of the air supplied to the treatment chamber 750 via the air supply line. Moreover, as previously mentioned, a flow control valve 752 may be coupled to the air supply line 800 to enable the flow rate of the air being supplied to the treatment chamber 750 to be controlled. In some embodiments, the flow control valve 752 may be automatically controlled via the controller 710. As previously mentioned, downstream of the flow control valve 752 the air is mixed with the ozone being supplied by the ozone generator 720, buffer chamber 730, and ozone cuvette 740 via the ozone injection valve 714. The air may be mixed with the ozone in the air supply line 800 via a turbulent flow regime present in the air supply line.

By precisely controlling the ozone concentration, ozone flow rate, air flow rate, temperature and humidity, gas having tightly controlled temperature, humidity, flow-rate, and ozone concentration can be obtained and maintained within the treatment chamber 750 so as to provide an effective sterilization of materials provided in the treatment chamber. As such, in one embodiment, there is no direct ozone concentration sensor or measurement taking place within the treatment chamber 750. Rather, the ozone concentration can be inferred by controlling the other parameters (e.g., flow-rates, temperature, humidity, ozone concentration in the buffer chamber). Alternatively, it is envisioned that an ozone concentration sensor could be installed within or coupled to the treatment chamber 750 for directly measuring the concentration of ozone within the treatment chamber 750.

Referring again to FIG. 1, in some embodiments the sterilization system 700 may include a cuvette blowing line 850 for zeroing the cuvette. That is, the cuvette blowing line 850 may allow the user, via the controller 710, to introduce air into the ozone cuvette 740 to flush out the ozone cuvette 740 prior to operation to remove residual gas/ozone from the cuvette 740.

It should be noted that during the second or treatment operating mode, ozone gas is being discharged from the treatment chamber 750 to the atmosphere via the ozone destructor 790.

It will be appreciated that although components described herein may be illustrated as separate or combined, they may readily be rearranged without departing from the scope of the present disclosure.

What is claimed is:

1. A sterilization system comprising:
   an ozone generator for generating a flow of ozone;
   a buffer chamber in fluid communication with the ozone generator, the buffer chamber for storing the flow of ozone received from the ozone generator;
   an ozone cuvette in fluid communication with the buffer chamber, the ozone cuvette for monitoring a concentration of ozone in a flow of ozone passing from the buffer chamber to the ozone cuvette;
   a treatment chamber for receiving a material for sterilization, the treatment chamber being in fluid communication with the ozone cuvette for receiving a flow of ozone from the ozone cuvette;
   one or more valves coupled between the buffer chamber and the ozone cuvette, and between the ozone cuvette and the treatment chamber, each valve being selectively movable between an open position and a closed position;
   a controller in communication with the one or more valves for selectively and independently moving each of the valves between the open and closed positions;
   wherein the sterilization system includes first and second operating modes, in the first operating mode, the treatment chamber is isolated from the ozone generator and the buffer chamber such that ozone is not being supplied to the treatment chamber, and in the second operating mode, the treatment chamber is in communication with the ozone generator and the buffer chamber such that ozone is being supplied to the treatment chamber and a flow of air is supplied to an air supply line in communication with the treatment chamber;
   the system further comprising:
   a blower and a flow meter coupled to the line of air for controlling a flow rate of the flow of air;
   a humidifier and an air cooler in fluid communication with the air supply line for monitoring and controlling a humidity and a temperature, respectively, of the air; and
   a flow control valve disposed in the air supply line, the flow control valve positioned downstream of the humidifier, the air cooler, the blower and the flow meter; wherein the flow of ozone is directed to the air supply line downstream of the flow control valve and upstream of the treatment chamber.

2. The system of claim 1, wherein, the ozone cuvette is communicatively coupled to the controller such that when the controller determines that an ozone concentration of the flow of ozone received by the ozone cuvette from the buffer chamber is equal to or greater than a predetermined concentration, the controller transitions the sterilization system from the first operating mode to the second operating mode.

3. The system of claim 2, wherein in the first operating mode, the controller selectively closes an ozone injection valve coupled between the ozone cuvette and the treatment chamber so that the flow of ozone to the treatment chamber is prevented, and the controller further selectively opens an ozone bypass valve coupled between the ozone cuvette and an ozone destructor so that the flow of ozone passes through the ozone destructor and then into the atmosphere.

4. The system of claim 3, wherein in the second operating mode, the controller selectively closes the ozone bypass valve and selectively opens the ozone injection valve so that ozone flows to the treatment chamber.

5. The system of claim 1, wherein the controller is programmed to execute instructions to control a flow rate of the flow of ozone, a flow rate of air being mixed with the flow of ozone, a temperature of the air, and a humidity of the air.

6. The system of claim 5, wherein the controller is programmed to execute instructions to automatically adjust the flow rate of the flow of ozone, the flow rate of air being mixed with the flow of ozone, the temperature of the air, and the humidity of the air to maintain a desired concentration and flowrate of the flow of ozone into the treatment chamber.

7. The system of claim 1, further comprising an air source for supplying a flow of air to the ozone generator, the ozone generator for converting the flow of air into the flow of ozone; wherein the air source includes a cylinder of compressed air, and the air source further comprises a concentrator to increase a level of oxygen in the flow of oxygen supplied to the ozone generator.

8. The system of claim 1, wherein in the first operating mode, the ozone generator continuously operates to supply the buffer chamber with the flow of ozone.

9. The system of claim 1, wherein a concentration of the flow of ozone stored in the buffer chamber is greater than a concentration of ozone provided to the treatment chamber.

10. The system of claim 9, wherein the concentration of the flow of ozone in the buffer chamber is approximately 10 times greater than the ozone concentration of the flow of ozone provided to the treatment chamber.

11. The system of claim 1, wherein the ozone cuvette continuously senses the concentration of the flow of ozone being supplied by the buffer chamber and provides sensed concentration information to the controller.

12. The system of claim 1, further comprising an ozone destructor to convert the flow of ozone back into oxygen; wherein in the first operating mode, the flow of ozone flows from the ozone cuvette to a second valve to an ozone bypass valve to the ozone destructor.

* * * * *